United States Patent
Jensen

(10) Patent No.: US 11,642,113 B2
(45) Date of Patent: May 9, 2023

(54) INTERVENTIONAL DEVICE FOR SPECIMEN RETRIEVAL

(71) Applicant: Urotech GmbH, Achenmühle (DE)

(72) Inventor: Jørgen Bjerggaard Jensen, Aarhus (DK)

(73) Assignee: Urotech GmbH, Rohrdorf OT Achenmühle (DK)

( * ) Notice: Subject to any disclaimer, the term of this patent is extended or adjusted under 35 U.S.C. 154(b) by 943 days.

(21) Appl. No.: 16/484,851

(22) PCT Filed: Feb. 13, 2018

(86) PCT No.: PCT/EP2018/053511
§ 371 (c)(1),
(2) Date: Aug. 9, 2019

(87) PCT Pub. No.: WO2018/149810
PCT Pub. Date: Aug. 23, 2018

(65) Prior Publication Data
US 2020/0060665 A1 Feb. 27, 2020

(30) Foreign Application Priority Data
Feb. 15, 2017 (DK) .......................... PA 2017 70102

(51) Int. Cl.
*A61B 17/00* (2006.01)
*A61B 17/221* (2006.01)
(Continued)

(52) U.S. Cl.
CPC .......... *A61B 17/00234* (2013.01); *A61B 1/07* (2013.01); *A61B 1/307* (2013.01);
(Continued)

(58) Field of Classification Search
CPC ............ A61B 17/221; A61B 17/00234; A61B 2017/2212; A61B 2017/00287; A61B 2017/00358; A61B 10/06; A61B 1/307
See application file for complete search history.

(56) References Cited

U.S. PATENT DOCUMENTS

2003/0199915 A1   10/2003  Shimm
2005/0033243 A1*  2/2005   Jespersen ......... A61B 17/00234
                                                         604/205
(Continued)

FOREIGN PATENT DOCUMENTS

EP     2497429 A1      9/2012
WO     2011049918 A1   4/2011

OTHER PUBLICATIONS

Van Der Heijden et al., "Phase II Marker Lesion Study With Intravesical Instillation of Apaziquone for Superficial Bladder Cancer: Toxicity and Marker Response", The Journal of Urology®, vol. 176, 1349-1353, Oct. 2006.
(Continued)

*Primary Examiner* — Diane D Yabut
(74) *Attorney, Agent, or Firm* — Taft Stettinius & Hollister LLP

(57) ABSTRACT

There is presented an interventional device (100), such as a device for minimally invasive surgery, comprising a bag arranged for being transformable between an open configuration and a closed configuration, a shaft (106), a grasper (108) mounted on a distal end of said shaft, wherein the bag further comprises a fluid passageway arranged so that in the closed configuration the fluid passageway enables that fluid may be expelled through the fluid passageway from an interior volume of the bag to an exterior volume of the bag and furthermore enables that a solid element above a predetermined threshold size may be retained in the bag. The fluid passageway may be advantageous for enabling that
(Continued)

liquid may be expelled from the bag while larger solid elements, such as a piece of a tumour, may be retained in the bag for removal from a body cavity.

32 Claims, 4 Drawing Sheets

(51) Int. Cl.
    *A61B 1/07*         (2006.01)
    *A61B 1/307*      (2006.01)
    *A61B 17/29*      (2006.01)

(52) U.S. Cl.
    CPC ............ *A61B 17/221* (2013.01); *A61B 17/29* (2013.01); *A61B 2017/00287* (2013.01); *A61B 2017/00358* (2013.01); *A61B 2017/2215* (2013.01)

(56) References Cited

U.S. PATENT DOCUMENTS

| | | |
|---|---|---|
| 2010/0152609 A1 | 6/2010 | Zwolinski et al. |
| 2010/0152612 A1 | 6/2010 | Headley, Jr. et al. |
| 2012/0203241 A1 | 8/2012 | Williamson, IV |
| 2016/0256144 A1 | 9/2016 | Menn et al. |
| 2017/0333061 A1* | 11/2017 | Atwell ................. A61B 17/221 |

OTHER PUBLICATIONS

Maurice et al., "Endoscopic Snare Resection of Bladder Tumors: Evaluation of an Alternative Technique for Blader Tumor Resection", The Journal of Endourology, vol. 26, No. 6, 614-617, Jun. 2012.
Naselli et al., Surgery Illustrated—Focus on Details En bloc transurethral resection of bladder lesions: a trick to retrieve specimens up to 4.5 cm, BJU International, vol. 109, 960-963, 2012.
International Search Report; European Patent Office; International Application No. PCT/EP2018/053511; dated Apr. 26, 2018; 4 pages.
Written Opinion of the International Searching Authority; European Patent Office; International Application No. PCT/EP2018/053511; dated Apr. 26, 2018; 8 pages.
International Preliminary Report on Patentability; European Patent Office; International Application No. PCT/EP2018/053511; dated Aug. 20, 2019; 9 pages.
European Office Action; European Patent Office; European Application No. 18705597.5; dated Oct. 4, 2022; 5 pages.

* cited by examiner

INTERVENTIONAL DEVICE FOR SPECIMEN RETRIEVAL

CROSS-REFERENCE TO RELATED APPLICATIONS

This application is a U.S. National Phase of International PCT Application No. PCT/EP2018/053511 filed on Feb. 13, 2018, which claims priority to Danish Patent Application No. PA 2017 70102 filed Feb. 15, 2017, each of which are incorporated herein by reference in their entirety.

FIELD OF THE INVENTION

The present invention relates to an interventional device for specimen retrieval and in particular relates to an interventional device with a grasper and a bag and a corresponding method.

BACKGROUND OF THE INVENTION

Tumours in the bladder may be resected and removed through the urethra via a resectoscope. This operation may be referred to as a transurethral resection of the bladder (TURB). Large tumours, such tumours with a largest dimension being 1 cm or more, cannot be removed in a single piece due to the limited size of the resectoscope. The tumour may then be removed by cutting it into pieces (during the resection) before removing it. Such cutting may be associated with an increased risk that the tumour may spread compared to resection in one piece (en bloc technique).

The reference US2010/0152609A1 describes a surgical instrument that can be used to capture and retrieve tissue, or other specimens, from within the body of a patient through a single trocar port.

An improved device and method for specimen retrieval would be advantageous, and in particular a simple device and method, which might enable removal of large bladder tumours without an increased risk of spreading would be advantageous.

SUMMARY OF THE INVENTION

It may be seen as an object of the present invention to provide a device and method that solves the above mentioned problems of the prior art with increased risk of spreading during removal of large bladder tumours. It is a further object of the present invention to provide an alternative to the prior art.

Thus, the above described object and several other objects are intended to be obtained in a first aspect of the invention by providing an interventional device, such as an elongated surgical device, such as an elongated surgical device for en bloc transurethral removal of bladder tumours, said interventional device comprising:
  a bag, such as a specimen retrieval bag, wherein said bag comprises a first opening and a second opening, and wherein said bag is arranged for being transformable between
    an open configuration, and
    a closed configuration wherein said second opening is smaller than in the open configuration, such as wherein the second opening is fluid-tight, such as wherein in the closed configuration said second opening is smaller than said first opening,
  a shaft, such as wherein the shaft defines an axis along a longitudinal direction of said shaft, wherein said shaft extends through said first opening,
  a grasper, wherein said grasper is mounted on a distal end of said shaft,
  wherein in the open configuration the second opening is movable relative to the first opening and the grasper between
    a first position wherein the second opening is on an opposite side of the first opening with respect to the grasper,
    a second position wherein the grasper is located between the second opening and the first opening,
  wherein the bag further comprises a fluid passageway arranged so that in the closed configuration the fluid passageway enables that fluid may be expelled through the fluid passageway from an interior volume of the bag to an exterior volume of the bag and furthermore enables that a solid element, such as a tumour or a piece of a tumour, above a predetermined threshold size may be retained in the bag.

The invention is particularly, but not exclusively, advantageous for obtaining an interventional device, such as a minimally invasive surgical device, such as for use in removing a specimen from within the body of a patient, such as for en bloc transurethral removal of a bladder tumour. An advantage may be that the interventional device enables minimal invasive surgery so as to enable performing the removal of the bladder through a body opening such as a urethra or an incision. Another advantage may be that the arrangement of the bag and the grasper enables that the tumour can be grasped and encapsulated in the bag, so as to avoid contact between the tumour and surrounding tissue during removal, such as contact between the tumour and the urethral wall.

Another possible advantage may be that the fluid passageway enables that enables that fluid may be expelled through the fluid passageway from an interior volume of the bag to an exterior volume of the bag, which in turn enables that once the tumour is encapsulated in the bag, excess fluid can be expelled. The bladder is typically filled with fluid and hence arranging the tumour in the bag typically entails that excess fluid is also placed in the bag. The excess fluid entails that the size of the bag is larger than necessary, which may complicate or render impossible removal of the bag with the tumour via the opening, such as a urethra. Therefore, it is advantageous that fluid can be expelled from the bag, such as by squeezing fluid from within the bag back into the bladder (such as the bladder outside of the bag).

Reference to fluid in this application is generally understood to be a reference to liquid, such as an aqueous solution. This may in particular be relevant in the context of the application in the bladder, which is typically filled with an aqueous solution.

Another possible advantage may be that the fluid passageway enables that a solid element, such as a tumour or a piece of a tumour, above a predetermined threshold size may be retained in the bag. This may be advantageous since it is avoided that a tumour or a piece of a tumour, such as solid tumour or a solid piece of a tumour, above a predetermined threshold size, can leave the bag. This renders it possible to safely expel fluid from the bag without risking that a solid tumour or a solid piece of a tumour above a predetermined threshold size, can leave the bag (during expelling of fluid from the bag). Furthermore, this solution is relatively simple to implement and operate and renders it unnecessary to include means for transporting excess fluid, such as transporting excess fluid from a distal end of the shaft to a proximal end of the shaft, such as a fluid channel extending from a distal end of the shaft to a proximal end of the shaft arranged in connection with a vacuum source.

An 'interventional device' is generally known in the art, and may include any one of an endoscope or a resectoscope, such as a cystoscope. The interventional device may comprise a tubular body through which the grasper and bag and shaft may move. The tubular body may be suitable for insertion into the bladder via the urethra. An outer diameter of the tubular body may 12 mm or less, such as 11 mm or less, such as 10 mm or less. An inner diameter of a channel in the tubular body (such as a working channel) may be equal to or less than the outer diameter minus 1 mm.

By a 'bag' may be understood an element comprising a flexible, fluid-tight material suitable for encapsulating a bladder tumour.

By the 'first opening' may be understood an opening through which the shaft may extend. The connection between the first opening and the shaft may be fluid-tight.

The 'second opening' is an opening, which may be open and closed. In the closed condition, the second opening is fluid-tight or substantially fluid-tight, such as fluid-tight so that little, if any, fluids can leak out of the bag through the second opening. The second opening may for practical purposes be considered fluid-tight in the closed condition. In the closed configuration said second opening is smaller than in the open configuration, such as the cross-sectional area of the second opening in the closed configuration being less than 50%, such as less than 25%, such as less than 10%, such as less than 5%, such as less than 2%, such as less than 1%, of the area of the second opening in the open configuration. In the closed configuration said second opening may be smaller than said first opening, such as so that less fluid per time unit can leave the bag via the second opening than via the first opening (for an equal differential pressure drop from the interior of the bag to the exterior of the bag). It is noted that the 'second opening' may be in a closed condition, and that in the closed condition it is strictly speaking not an 'opening' and it may further be noted that the 'second opening' may in general be referred to interchangeably with 'port' or 'second port'. In case 'second opening' is referred to as 'port', then the 'first opening' may be referred to as 'opening'.

The 'shaft' may be an elongated element suitable for fitting into an interior volume (working channel) of the tubular body. The shaft extends through the first opening, so that the first opening surrounds the shaft.

By a 'grasper' is understood an element which is suitable for grasping and holding on to a bladder tumour. The grasper may comprise a loop a forceps or a 4-wire construction for a in a helical-wire design, such as a Dormia® from the company Coloplast.

In the open configuration the second opening is movable relative to the first opening and the grasper between a first position wherein the second opening is on an opposite side of the first opening with respect to the grasper, and a second position wherein the grasper is located between the second opening and the first opening. This may be advantageous in that in the first position, the second opening (and optionally some or all of the material of the bag) is on an opposite side of the first opening, such as a position of attachment of the bag to the shaft, with respect to the grasper. In other words, the bag is out of the way of the grasper, so that the bag does not obstruct the process of grasping the bladder tumour with the grasper. In the second position, the bladder tumour may be encapsulated in the bag by closing the second opening.

The change in position of second opening from the first position to the second position and/or the change in configuration from open to closed and/or orientation of the bag and/or changing the relative positions of the first opening and the second opening may be carried out in a manner similar to the manner described in the reference US2010/0152609A1 which is hereby included by reference in entirety (and in particular reference is made to FIGS. 5-8 and corresponding description (relating to the change in position of second opening from the first position to the second position) and to FIGS. 8-9 (relating to the change in configuration from open to closed) and to FIGS. 10-11 (relating to orientation of the bag and/or changing the relative positions of the first opening and the second opening)).

By 'the bag comprises a fluid passageway' may be understood that the bag comprises one or more openings through which fluid may pass. The fluid passageway may for example comprise one or more of a plurality of openings (such as holes), one or more openings with a filter or a sieve. The fluid passageway is arranged so that in the closed configuration the fluid passageway enables that fluid may be expelled through the fluid passageway from an interior volume of the bag to an exterior volume of the bag. This may be advantageous for ensuring that a predetermined fluid passageway is provided. Thus, the second opening can be closed, such completely closed, in a controllable manner, while the fluid passageway ensures that fluid can be expelled. In an embodiment, the fluid passageway is arranged so that a larger amount of fluid can pass through the fluid passageway than the second opening in the closed configuration.

The fluid passageway furthermore enables that a solid element, such as a tumour or a piece of a tumour, above a predetermined threshold size may be retained in the bag. An advantage of this may be that large chunks of solid tumour material is retained in the bag even if fluid is expelled. Another possible advantage may be that a relatively simple device may be provided, because the fluid passageway ensures both that fluid may be expelled via a fluid passageway, such as a hole in the bag, i.e., in a very simple manner (which may facilitate en bloc removal of, e.g., a bladder tumour) and that large pieces of tumour are retained in the bag (so as to avoid leaving behind large pieces of tumour, e.g., in the bladder), i.e., it is ensured in a very simple manner that larger pieces (i.e., above threshold size) of tumour does not leave the bag during expelling of liquid.

By 'threshold size' may be understood a size (of a solid element, such as an incompressible solid element), beyond which (such as when the solid element is larger than the threshold size) the solid element cannot pass through the fluid passageway. For the purpose of quantification, the threshold size is defined with reference to a circular hole, so that for any threshold size, a solid element, such as an incompressible solid element, is beyond (such as larger than) the threshold size if it cannot pass through a circular hole with a diameter corresponding to the threshold size. Thus, the unit of threshold size is length, and may for example be measured in millimetres (mm). For example, the threshold size may be 1 mm. If the threshold size is 1 mm, then any solid element, such as any incompressible solid element, which has a (sufficiently large) size so that it cannot pass through a circular hole with a diameter of 1 mm is retained (due to said element being beyond the threshold size).

By 'predetermined (threshold size)' may be understood that the threshold size is predetermined in the sense that it is defined by structural features of the interventional device, such as the structural features around the fluid passageway. The 'predetermined (threshold size)' may be independent of the configuration of the bag (such as independent of whether the bag is open or closed). For example, the threshold size may be (pre-)determined by the (structural) features of the size of the holes in a sieve, the pore size of a filter and/or one or more holes/openings (such as the holes openings associated with the first opening and/or being separated from the first opening and the second opening) in the bag. An advantage of such predetermined threshold size may be that it enables controlling the size of the solid elements which are allowed to leave the bag (for example by closing the second end completely or almost completely and expelling fluid— and possibly solid elements below the threshold size—via the fluid passageway (where the fluid passageway has well-defined openings ensuring that only solid elements below the predetermined threshold size can escape the bag)). In the present application threshold size and predetermined threshold size are used interchangeably and the threshold size is generally understood to be the predetermined threshold size.

In an embodiment there is presented an interventional device wherein the fluid passageway is placed in a first end of the bag, where said first end of the bag comprises the first opening, such as wherein a second end of the bag comprises the second opening, such as wherein a border between the second and first end of the bag is located at an interface where a length to each of the first opening and the second opening is equal in a configuration of maximum distance between the first opening and the second opening. An advantage of this may be that it enables that the second end (with the second opening) of the bag can be at least partially drawn into the tubular body while the first end is outside. This may in turn yield the advantage that fluid can be expelled from the bag, in which case any leakage from the second opening will enter into the tubular body (where it does no harm) and fluid expelled via the fluid passageway will be expelled into the bladder (and not into the wall of the urethra).

In an embodiment there is presented an interventional device wherein the fluid passageway comprises a separation element being positioned in a separation opening. An advantage of this may be that it provides an embodiment for realizing a fluid passageway while still retaining solid elements above the threshold size. Another possible advantage may be that a cross-sectional area of the fluid passageway may be large, because, e.g., a filter or a sieve, may comprise many (small) openings, which in turn enable that a large amount of fluid can quickly be expelled without applying a large pressure differential. By a 'separation element' may be understood any element which is suitable for passing fluid while separating (retaining) solid elements above the threshold size, such as a filter or a sieve. By 'separation opening' may be understood an opening, such as a hole, in which the separation element can be placed.

In a further embodiment there is presented an interventional device wherein the separation element is a filter or a sieve. The filter may comprise a pore size (diameter) corresponding to the threshold size. The sieve may comprise openings, such as circular openings, with a size (diameter) corresponding to the threshold size. For example if the threshold size is 1 mm, then the diameter of the pores or the diameter of the openings may also be 1 mm.

In an embodiment there is presented an interventional device wherein the fluid passageway comprises one or more separation openings in the bag. An advantage of having more separation openings may be that it enables expelling more fluid per unit of time for an equivalent pressure differential (compared to a situation with only one separation opening). In embodiments, each separation opening is a hole, such as circular hole, with a diameter corresponding to the threshold size (for example if the threshold size is 1 mm, then the diameter of the hole is 1 mm).

In an embodiment there is presented an interventional device wherein a cross-sectional area of the fluid passageway is given by $pi*(threshold\ size/2)^2$ or more, such as $2*pi*(threshold\ size/2)^2$ or more, such as $5*pi*(threshold\ size/2)^2$ or more, such as $10*pi*(threshold\ size/2)^2$ or more, such as $20*pi*(threshold\ size/2)^2$ or more. An advantage of having the cross-sectional area being larger than $pi*(threshold\ size/2)^2$ may be that it enables expelling more fluid per unit of time for an equivalent pressure differential (compared to a situation where the cross-sectional area is $pi*(threshold\ size/2)^2$ or less).

In an embodiment there is presented an interventional device wherein the predetermined threshold size is 1 mm, such as 0.75 mm, such as 0.5 mm, such as 0.25 mm, such as 0.1 mm. An advantage of this may be that only treatable tumour pieces can leave the bag (and end up, at least temporarily, in the bladder) upon removal of a resected tumour with the interventional device. A piece of a tumour with a size less than 1 mm (such as said piece of tumour not being able to pass through a circular hole with 1 mm in diameter) can be eradicated with post-operative single installation of intra-vesical chemotherapy. A possible advantage of this is thus that for a patient with a piece of a bladder tumour with a size of 1 mm or less (which has left the bag during removal of a resected tumour and has thus ended up in the bladder), it may be possible to treat the patient, such as treat the patient with chemotherapy (as described in the reference "*Phase II Marker Lesion Study With Intravesical Instillation of Apaziquone for Superficial Bladder Cancer: Toxicity and Marker Response*" by Antoine G. van der Heijden et al., THE JOURNAL OF UROLOGY®, Vol. 176, 1349-1353, October 2006, which is hereby included by reference in entirety).

In an embodiment there is presented an interventional device wherein the shaft is at least partially placed inside an elongated tubular body, such as a resectoscope, and wherein the shaft is arranged for extending through a distal opening of said tubular body so that the grasper is outside of the tubular body at the distal end of the tubular body, and when the first opening is outside of the elongated tubular body, the second opening is in the second position, and said bag is in the closed configuration, the second opening may be brought closer to the distal opening than the first opening.

An advantage of this may be that bag can be withdrawn from the bladder through the urethra with the second opening in front (such as the second opening exiting first). In a particular embodiment, the second opening may furthermore be brought into the tubular body (such as wherein the first opening is outside of the tubular body). This may yield the advantage, that if the second opening leaks, then any leaking fluid may leak into the tubular body where it does not harm.

In an embodiment there is presented an interventional device wherein the bag is elongated. An advantage of this may be that the bag can more easily be brought out through the urethra. By 'elongated' may in this context be understood that a maximum distance from the first opening to the second opening is larger than a maximal distance from one side of the bag to the other side of the bag in a direction being orthogonal to a direction from the first opening to the second opening.

In an embodiment there is presented an interventional device wherein the separation opening is the first opening. Thus, the connection between the bag and the shaft at the first opening is not fluid-tight. The first opening double functions as the fluid passageway and the opening for the shaft. An advantage of this may be that the first opening double functions, such as enabling that the bag can be kept relatively simple with only two openings. In an alternative embodiment, the bag comprises at least three openings, such as the first opening, the second opening and a separation opening being distinct from the first opening and the second opening.

In an embodiment there is presented an interventional device wherein the grasper and the bag may be inserted and operated and removed through a single body opening, such as a natural body opening or an incision. An advantage of this may be that only one body opening, such as a natural body opening is necessary.

In an embodiment there is presented an interventional device wherein the grasper is suitable for grasping a bladder tumour (such as a bladder tumour having a size along a largest dimension from 5 mm to 5 cm), such as thereby enabling that the grapping means can grab the tumour in entirety and put the tumour in the bag. In an embodiment there is presented an interventional device wherein the second opening is large enough in the open configuration to accommodate passage of a bladder tumour, such as thereby enabling that the grapping means can grab the tumour in entirety and put the tumour in the bag. In an embodiment there is presented an interventional device wherein the bag is large enough in the closed configuration to encapsulate a bladder tumour, such as thereby enabling that the grapping means can grab the tumour in entirety and put the tumour in the bag. In an embodiment there is presented an interventional device wherein the interventional device comprises a snare loop for transforming said bag between the open configuration and the closed configuration, such as from the open configuration to the closed configuration.

In an embodiment there is presented an interventional device wherein the grasper is chosen from the group comprising, such as consisting of:
  a forceps, and
  a loop.

In an embodiment there is presented an interventional device furthermore comprising fibre optic system for enabling imaging at the distal end of the shaft, wherein the bag may be partially or fully removed from a field of view of the fibre optic system. An advantage of this may be that an operator can visually monitor the process. Having the interventional device arranged so that the bag may be partially or fully removed from the field of view may be realized by arranging an optical axis of the fibre optic system so that it is outside of the bag. Another alternative (in addition to forces and loop) may comprise a corkscrew.

According to a second aspect there is presented a method for removing a solid element from a cavity through an opening of the cavity, said method comprising:
  a. Providing an interventional device according to any one of the preceding claims,
  b. Inserting the distal end of the interventional device into the cavity via the opening,
  c. Arranging the bag in the open configuration,
  d. Arranging the second opening in the first position,
  e. Grasping the solid element with the grasper,
  f. Arranging the second opening in the second position,
  g. Arranging the bag in the closed configuration.
  h. Withdraw the interventional device with the solid element from the cavity via the opening.

In an embodiment there is presented an interventional device wherein the solid element is a bladder tumour or a piece of a bladder tumour, wherein the cavity is a bladder and wherein the opening is a urethra.

The first and second aspect of the present invention may each be combined with any of the other aspects. These and other aspects of the invention will be apparent from and elucidated with reference to the embodiments described hereinafter.

BRIEF DESCRIPTION OF THE FIGURES

The interventional device and the method for removing a solid element from a cavity through an opening of the cavity according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1:
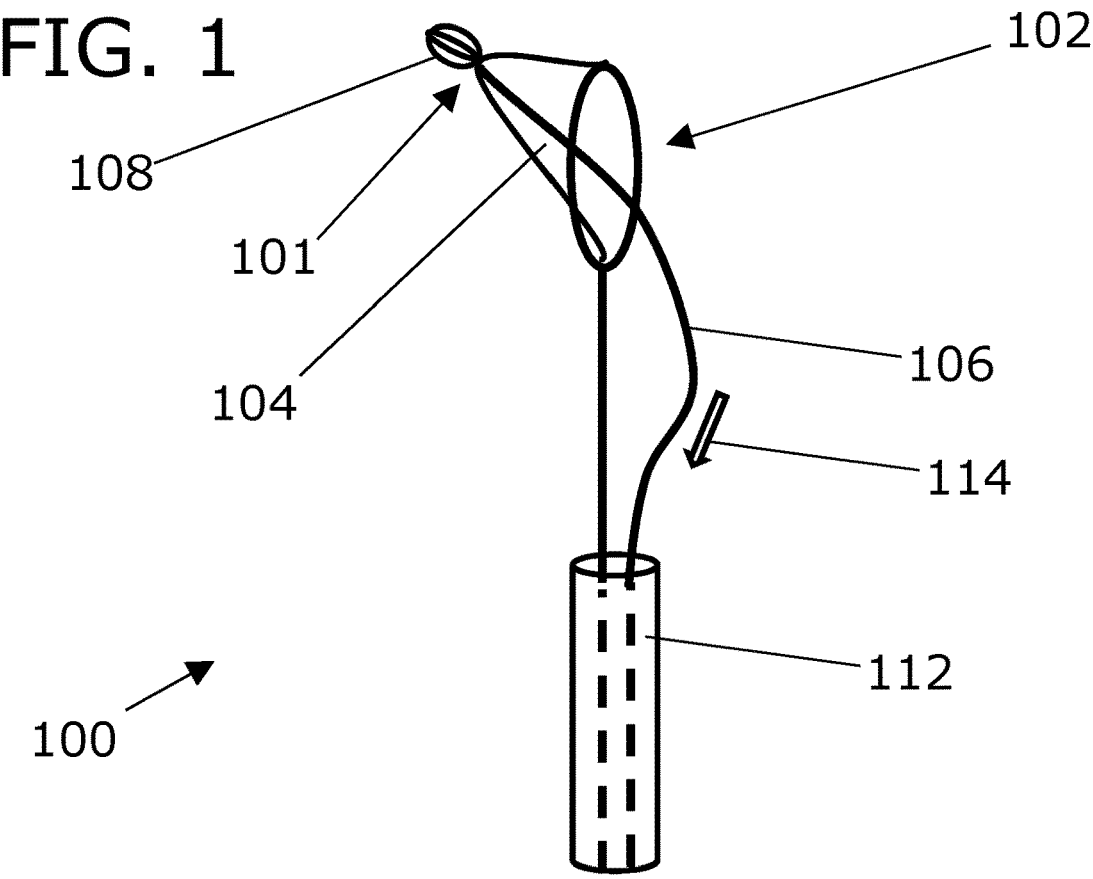
FIG. 1 shows an interventional device with the bag in the open configuration and the second opening in the first position.

FIG. 1 shows an interventional device 100 which is an elongated surgical device for en bloc transurethral removal of bladder tumours via minimally invasive surgery, said interventional device comprising:
  a specimen retrieval bag 104 wherein said bag comprises a first opening 101 and a second opening 102, and wherein said bag is arranged for being transformable between
    an open configuration, and
    a closed configuration wherein said second opening (102) is smaller than in the open configuration, such as wherein in the closed configuration said second opening is smaller than said first opening.

In FIG. 1, the bag 104 is shown in the open configuration. FIG. 1 furthermore shows
  a shaft 106 which defines an axis along a longitudinal direction of said shaft, wherein said shaft extends through said first opening 101,
  a grasper (108), wherein said grasper is mounted on a distal end of said shaft,
  wherein in the open configuration the second opening (102) is movable relative to the first opening (101) and the grasper (108) between a first position wherein the second opening (102) is on an opposite side of the first opening (101) with respect to the grasper (108), a second position wherein the grasper (108) is located between the second opening (102) and the first opening (101).

In FIG. 1, the second opening is in the first position. The figure shows that in this first position, the second opening 102 and the bag 104 is out of the way of the grasper 108, so that it is less complicated for an operator to grasp and hold on to a tumour. FIG. 1 also shows a tubular element 112. The position of the grasper 108 on shaft 106 can be moved via moving the shaft 106 along its axis as indicated by arrow 114. Thereby the second opening can be moved into the second position (relative to the grasper 108 and the first opening 101).

Figure 2:
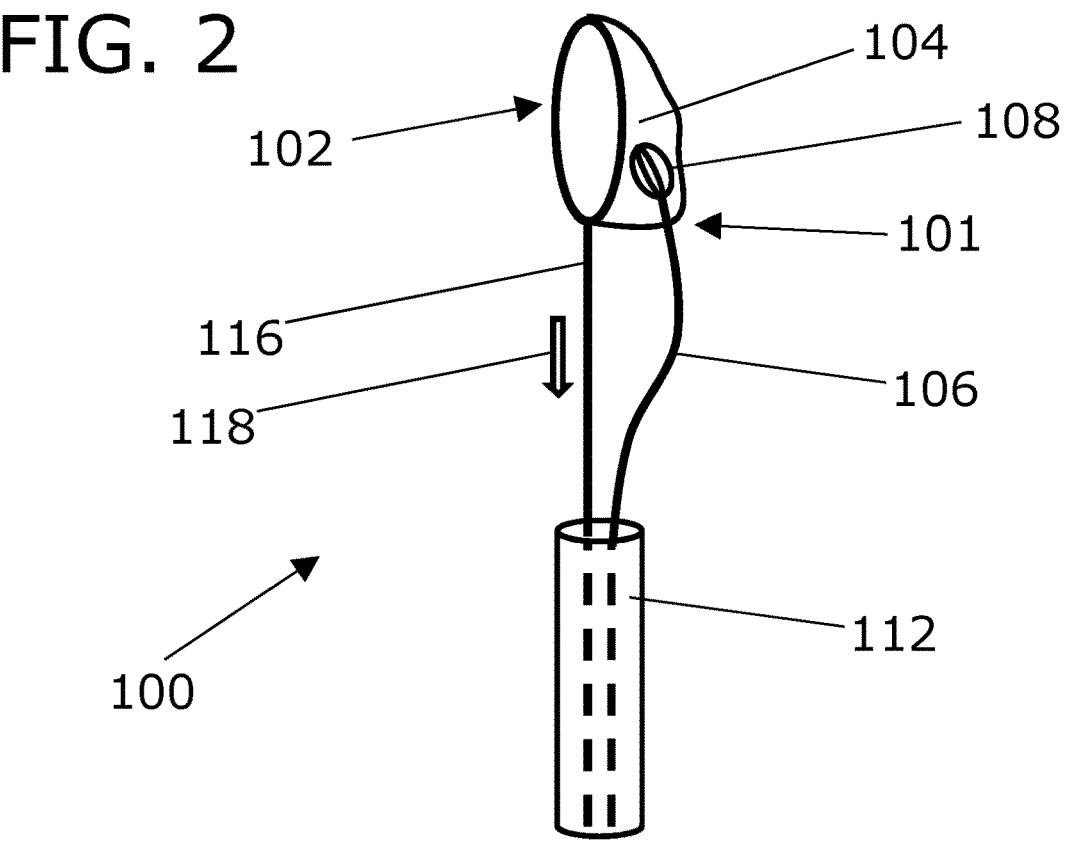
FIG. 2 shows an interventional device with the bag in the open configuration and the second opening in the second position.

FIG. 2 shows the interventional device 100 of FIG. 1, but in FIG. 2, the second opening 102 is in the second position. It can be seen that in this position, the bag 104 can be brought to encapsulate a tumour (held by the grasper 108) by closing the second opening 102. The second opening can be brought closer the distal opening of the tubular element by moving the shaft 116 of the second opening 102 in the direction indicated by the arrow 118.

Figure 3:
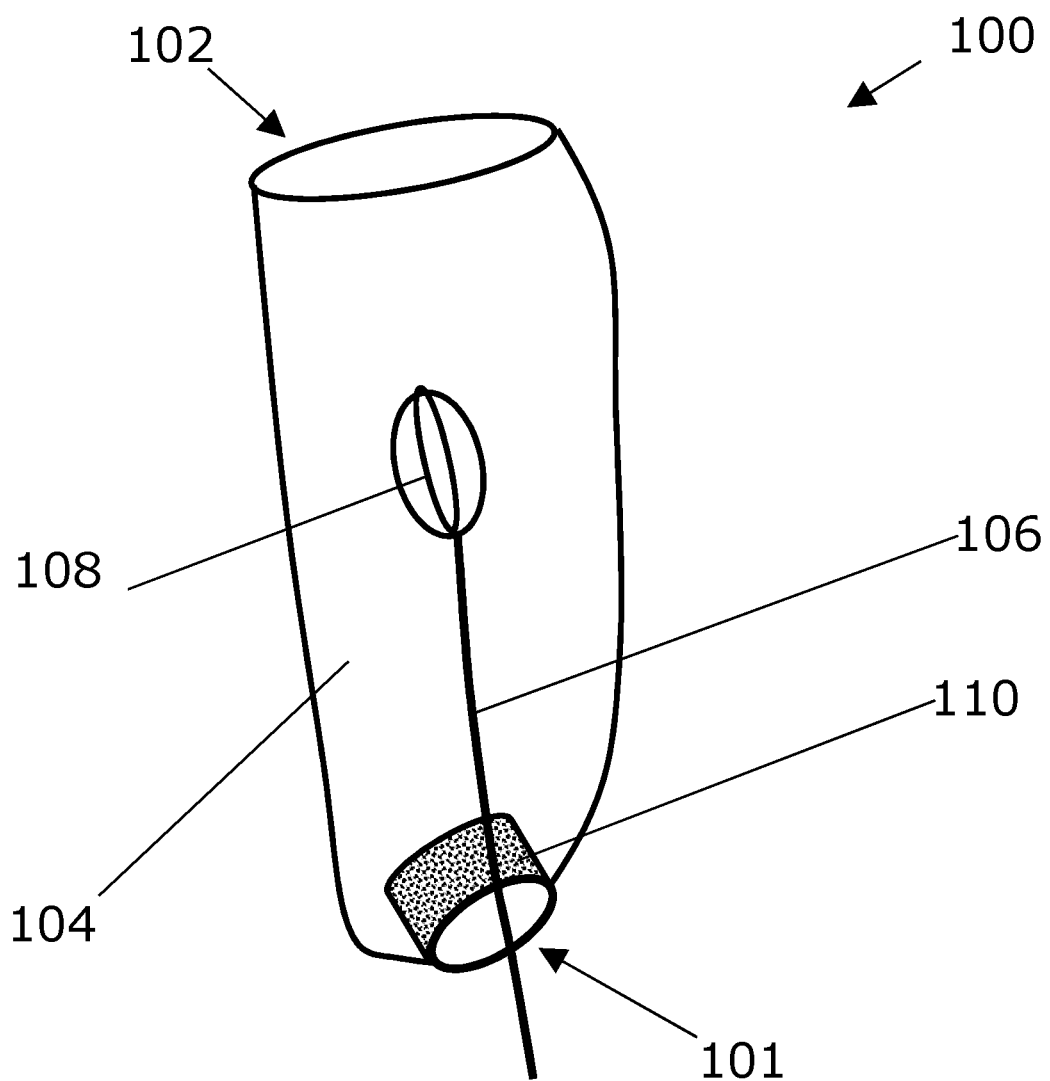
FIG. 3 shows an interventional device with a separation element.

FIG. 3 shows the interventional device 100 of FIGS. 1-2, but FIG. 3 focuses on the part with the first opening. In the present embodiment, the connection between the shaft 106 and the first opening 101 is not fluid-tight and the fluid passageway is given by this lack of fluid-tightness which may be described as a separation opening. FIG. 3 thus shows that the bag 104 further comprises a fluid passageway arranged so that in the closed configuration the fluid passageway enables that fluid may be expelled through the fluid passageway from an interior volume of the bag to an exterior volume of the bag and furthermore enables that a solid element, such as a tumour or a piece of a tumour, above a threshold size may be retained in the bag 104. More particularly, the fluid passageway comprises a separation element 110 in the form of a filter (in the form of a sponge) being positioned in the separation opening.

Figure 4:
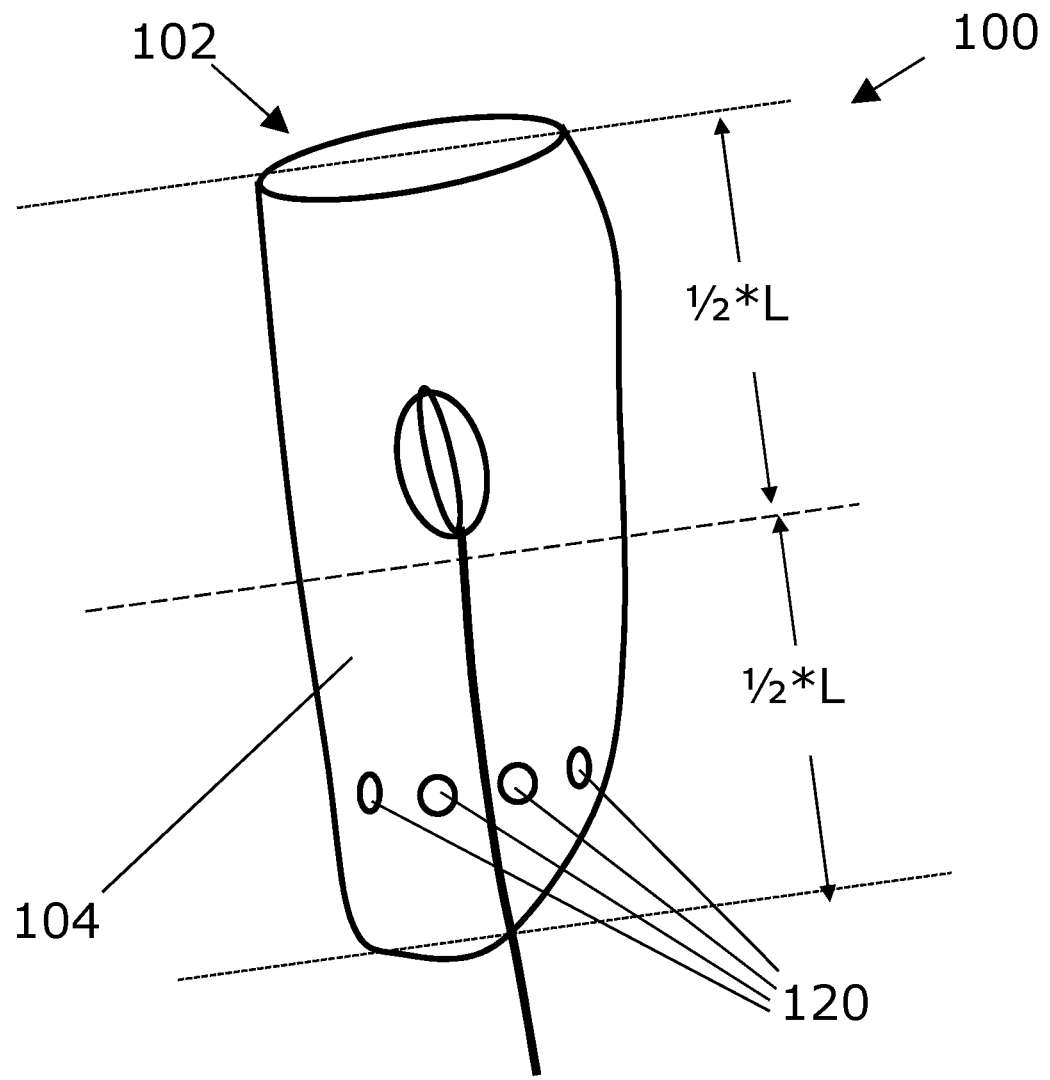
FIG. 4 shows an embodiment wherein the first opening is fluid-tight and the fluid passageway is realised via a plurality of holes.

FIG. 4 shows a similar embodiment as in FIGS. 1-3, but wherein the first opening is fluid-tight and the fluid passageway is realised via a plurality of holes 120, where each hole has a diameter which corresponds to the threshold size. The dotted (upper and lower) lines indicate the position of first opening and the second opening, respectively, and the dashed (middle) line indicates the position which is equidistantly placed with respect to the first opening and the second opening (both being half the length L of the bag away), hence the dashed (middle) line indicates the border between the first end and the second end.

Figure 5:
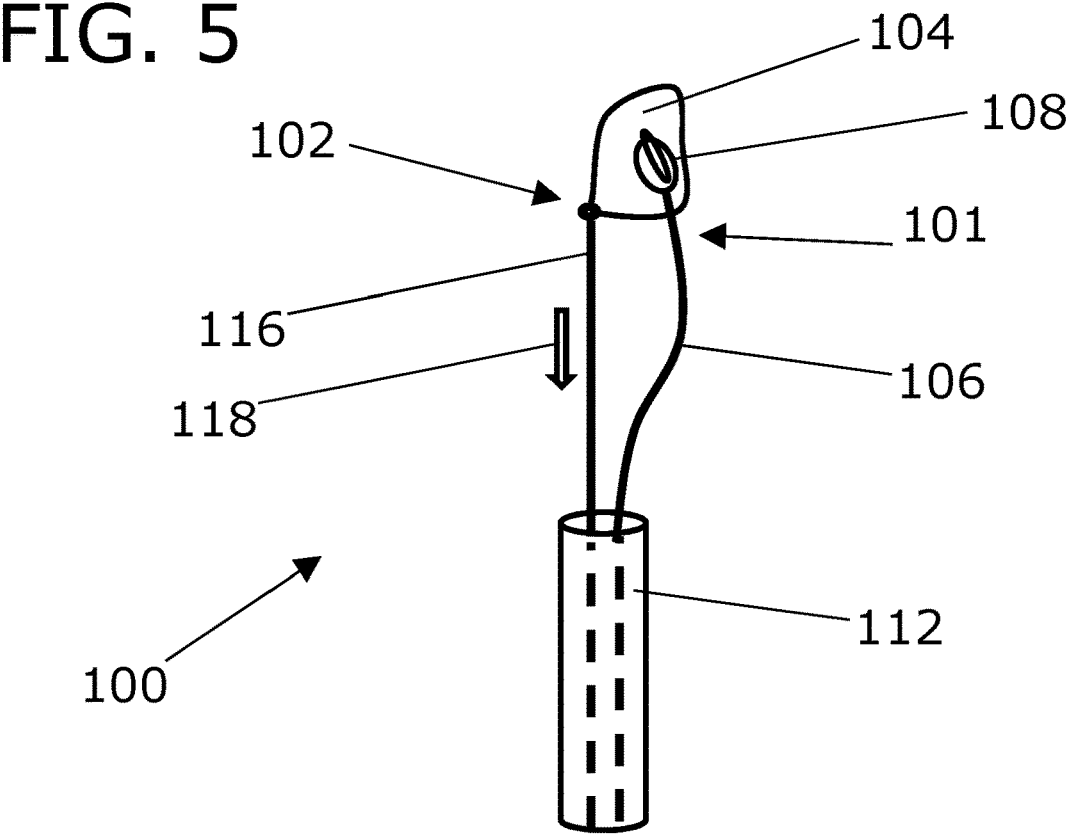
FIG. 5 shows an embodiment similar to FIG. 2, but wherein the bag is in the closed configuration and the second opening is fluid-tight so that little, if any, fluids can leak out of the bag through the second opening.

FIG. 5 shows an embodiment similar to FIG. 2, but wherein the bag is in the closed configuration and the second opening is fluid-tight so that little, if any, fluid can leak out of the bag through the second opening. The second opening can be brought closer to the distal end of the tubular element 112 by moving the shaft 116 of the second opening 102 in the direction indicated by the arrow 118.

Figure 6:
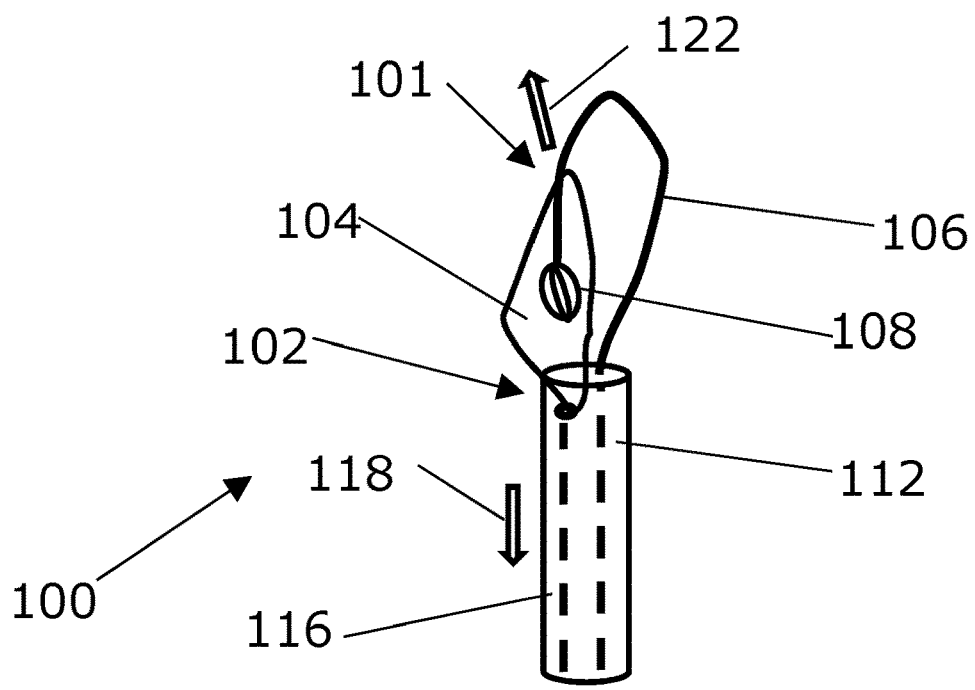
FIG. 6 shows an embodiment similar to FIG. 5 except that the second opening is brought closer to the distal end of the tubular body than the first opening.

FIG. 6 shows an embodiment similar to FIG. 5 except that the second opening has been brought closer to the distal end of the tubular element 112 than the first end 101 (in particular wherein the second 102 end inside the tubular element 112 while the first end 101 is outside of the tubular element 112) by moving the shaft 116 of the second opening 102 in the direction indicated by the arrow 118. is brought closer to the distal end of the tubular body than the first opening. Any liquid leaked form the second end 102 ends up in the tubular body 112. Any liquid expelled from the fluid passageway (which in this embodiment is placed at the first end, such as in connection with the first opening 101) is ends up in the cavity from which the bag is removed as indicated by arrow 124, for example a bladder. Removal may be carried out by moving the entire device as depicted in FIG. 6 in the direction of FIG. 118.

To sum up, there is presented an interventional device (100), such as a device for minimally invasive surgery, comprising a bag arranged for being transformable between an open configuration and a closed configuration, a shaft (106), a grasper (108) mounted on a distal end of said shaft, wherein the bag further comprises a fluid passageway arranged so that in the closed configuration the fluid passageway enables that fluid may be expelled through the fluid passageway from an interior volume of the bag to an exterior volume of the bag and furthermore enables that a solid element above a predetermined threshold size may be retained in the bag. The fluid passageway may be advantageous for enabling that liquid may be expelled from the bag while larger solid elements, such as a piece of a tumour, may be retained in the bag for removal from a body cavity.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An interventional device, said interventional device comprising:
   a bag, wherein said bag comprises a first opening and a second opening, and wherein said bag is arranged for being transformable between:
      an open configuration, and
      a closed configuration wherein said second opening is smaller than in the open configuration;
   a shaft, wherein said shaft extends through said first opening of the bag;
   a grasper, wherein said grasper is mounted on a distal end of said shaft;
   wherein in the open configuration of the bag, the second opening is movable relative to the first opening and the grasper, the second opening is movable between (i) a first position wherein the second opening is on an opposite side of the first opening with respect to the grasper, and (ii) a second position wherein the grasper is located between the second opening and the first opening;
   wherein the bag further comprises a fluid passageway arranged so that the bag in the closed configuration enables the fluid passageway to expel fluid through the fluid passageway from an interior volume of the bag to an exterior volume of the bag and furthermore enables a solid element above a predetermined threshold size to be retained in the bag;

an elongated tubular body having a distal opening at a distal end, the shaft is at least partially placed inside the elongated tubular body wherein the shaft is arranged to extend through the distal opening so that the grasper is outside of the elongated tubular body at the distal end of the elongated tubular body;

wherein in the closed configuration of the bag:
the first opening is positioned outside of the elongated tubular body, and the second opening is in the second position that further corresponds to the second opening being in a fluid-tight configuration;
wherein the second opening may be positioned closer to the distal opening of the elongated tubular body than the first opening of the bag, wherein the fluid passageway includes the first opening configured to expel fluid from the first opening into a body cavity from which the bag is removed.

2. The interventional device according to claim 1, wherein the interventional device is an elongated surgical device.

3. The interventional device according to claim 2, wherein the elongated surgical device is an elongated surgical device for en bloc transurethral removal of bladder tumors.

4. The interventional device according to claim 1, wherein the bag is a specimen retrieval bag.

5. The interventional device according to claim 1, wherein for the closed configuration said second opening is smaller than said first opening.

6. The interventional device according to claim 1, wherein the shaft defines an axis along a longitudinal direction of said shaft.

7. The interventional device according to claim 1, wherein the solid element is a tumor or a piece of a tumor.

8. The interventional device according to claim 1, wherein the fluid passageway is placed in a first end of the bag, where said first end of the bag comprises the first opening.

9. The interventional device according to claim 8, wherein a second end of the bag comprises the second opening.

10. The interventional device according to claim 9, wherein a border between the second end and the first end of the bag is located at an interface where a length to each of the first opening and the second opening is equal in a configuration of maximum distance between the first opening and the second opening.

11. The interventional device according to claim 1, wherein the fluid passageway comprises a separation element being positioned in a separation opening.

12. The interventional device according to claim 11, wherein the separation element is a filter or a sieve.

13. The interventional device according to claim 11, wherein the separation opening is the first opening.

14. The interventional device according to claim 1, wherein the fluid passageway comprises one or more separation openings in the bag.

15. The interventional device according to claim 1, wherein a cross-sectional area of the fluid passageway is given by $pi*(threshold\ size/2)^2$ or more.

16. The interventional device according to claim 1, wherein a cross-sectional area of the fluid passageway is given by $2*pi*(threshold\ size/2)^2$ or more.

17. The interventional device according to claim 1, wherein a cross-sectional area of the fluid passageway is given by $5*pi*(threshold\ size/2)^2$ or more.

18. The interventional device according to claim 1, wherein a cross-sectional area of the fluid passageway is given by $10*pi*(threshold\ size/2)^2$ or more.

19. The interventional device according to claim 1, wherein a cross-sectional area of the fluid passageway is given by $20*pi*(threshold\ size/2)^2$ or more.

20. The interventional device according to claim 1, wherein the predetermined threshold size is 1 mm.

21. The interventional device according to claim 1, wherein the predetermined threshold size is 0.75 mm.

22. The interventional device according to claim 1, wherein the predetermined threshold size is 0.5 mm.

23. The interventional device according to claim 1, wherein the predetermined threshold size is 0.25 mm.

24. The interventional device according to claim 1, wherein the elongated tubular body is a resectoscope.

25. The interventional device according to claim 1, wherein the bag is elongated.

26. The interventional device according to claim 1, wherein the grasper and the bag may be inserted and operated and removed through a single body opening.

27. The interventional device according to claim 26, wherein the single body opening is a natural body opening or an incision.

28. The interventional device according to claim 1, wherein the grasper is chosen from the group comprising:
a forceps, and
a loop.

29. The interventional device according to claim 1, wherein the grasper is chosen from the group consisting of:
a forceps, and
a loop.

30. The interventional device according to claim 1, furthermore comprising a fibre optic system for enabling imaging at the distal end of the shaft, wherein the bag may be partially or fully removed from a field of view of the fibre optic system.

31. A method for removing a solid element from a cavity through an opening of the cavity, said method comprising:
a. Providing an interventional device according to claim 1,
b. Inserting the distal end of the interventional device into the cavity via the opening,
c. Arranging the bag in the open configuration,
d. Arranging the second opening in the first position,
e. Grasping the solid element with the grasper,
f. Arranging the second opening in the second position,
g. Arranging the bag in the closed configuration,
h. Withdrawing the interventional device with the solid element from the cavity via the opening.

32. The method according to claim 31, wherein the solid element is a bladder tumor or a piece of a bladder tumor, wherein the cavity is a bladder and wherein the opening is a urethra.

* * * * *